US007507861B2

(12) United States Patent
Castelli et al.

(10) Patent No.: US 7,507,861 B2
(45) Date of Patent: *Mar. 24, 2009

(54) PROCESS FOR THE PREPARATION OF ATOMOXETINE HYDROCHLORIDE

(75) Inventors: Eugenio Castelli, Arlate di Calco (IT); Giuseppe Lo Monaco, Seregno (IT); Silvia Mantovani, Cesano Maderno (IT); Paola Daverio, Villasanta (IT); Paolo Riva, Monza (IT); Alessandra Vailati, Seregno (IT); Stefano Bianchi, Como (IT)

(73) Assignee: Teva Pharmaceutical Fine Chemicals, S.r.l., Bulciago (LC) (IT)

( * ) Notice: Subject to any disclaimer, the term of this patent is extended or adjusted under 35 U.S.C. 154(b) by 65 days.

This patent is subject to a terminal disclaimer.

(21) Appl. No.: 11/169,995

(22) Filed: Jun. 28, 2005

(65) Prior Publication Data

US 2006/0009489 A1  Jan. 12, 2006

Related U.S. Application Data

(60) Provisional application No. 60/690,738, filed on Jun. 14, 2005, provisional application No. 60/689,778, filed on Jun. 9, 2005, provisional application No. 60/675,369, filed on Apr. 26, 2005, provisional application No. 60/666,666, filed on Mar. 30, 2005, provisional application No. 60/652,331, filed on Feb. 11, 2005, provisional application No. 60/652,332, filed on Feb. 11, 2005, provisional application No. 60/652,330, filed on Feb. 11, 2005, provisional application No. 60/622,065, filed on Oct. 25, 2004, provisional application No. 60/609,716, filed on Sep. 14, 2004, provisional application No. 60/583,641, filed on Jun. 28, 2004, provisional application No. 60/583,644, filed on Jun. 28, 2004, provisional application No. 60/583,643, filed on Jun. 28, 2004.

(51) Int. Cl.
*C07C 213/06* (2006.01)

(52) U.S. Cl. ........................ 564/347; 564/438

(58) Field of Classification Search .................. None
See application file for complete search history.

(56) References Cited

U.S. PATENT DOCUMENTS 4,018,895 A     4/1977  Molloy et al.
4,194,009 A  *  3/1980  Molloy et al. ............... 514/651
4,777,291 A    10/1988  Misner
4,868,344 A     9/1989  Brown
4,970,232 A  * 11/1990  Jakobsen et al. ............. 514/466
5,019,592 A  *  5/1991  Jakobsen et al. ............. 514/524
5,658,590 A     8/1997  Heiligenstein et al.
6,333,198 B1   12/2001  Edmeades et al.
6,541,668 B1    4/2003  Kjell et al.

FOREIGN PATENT DOCUMENTS

DE   41 23 253 A1      1/1993
EP   0 052 492 A1      5/1982
EP   0 193 405 A1      9/1986
EP   0 721 777 A2      1/1995
WO   WO 94/00416       1/1994
WO   WO 00/58262      10/2000
WO   WO 00/64855      11/2000
WO   WO 2006/004923 A2  1/2006
WO   WO 2006/004977 A2  1/2006
WO   WO 2006/004979 A2  1/2006
WO   WO 2006/020348 A2  2/2006
WO   WO 2006/068662 A1  6/2006

OTHER PUBLICATIONS

Anon (R)-(−)-N-Methyl-3-(2-Methylphenoxy)Phenyl-3-Phenylpropylamine (S)-(+)-Mandelate Chemical Abstracts Service XP-002367856 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 0, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modern Liquid Chromatography, 2nd ed. (John Wiley & Sons: New York 1979)—p. 549-552, 571-572.
Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

* cited by examiner

*Primary Examiner*—Brian J Davis
(74) *Attorney, Agent, or Firm*—Kenyon & Kenyon LLP

(57) ABSTRACT

The present invention provides improved processes for the preparation of atomoxetine hydrochloride under reaction conditions that improve reaction yields and facilitate commercial synthesis. In particular, the invention is directed to the synthesis of atomoxetine HCl by adding HCl to a mixture of (R)-(−)-tomoxetine (S)-(+)-mandelate with an organic solvent, with or without a base and water.

23 Claims, No Drawings

PROCESS FOR THE PREPARATION OF ATOMOXETINE HYDROCHLORIDE

CROSS-REFERENCE TO RELATED APPLICATIONS

This application claims the benefits of U.S. Provisional Patent Application Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332, filed Feb. 11, 2005, 60/583,643, filed Jun. 28, 2004, 60/652,331, filed Feb. 11, 2005, 60/666,666, filed Mar. 30, 2005, 60/675,369, filed Apr. 26, 2005, 60/689,778, filed Jun. 9, 2005, and 60/690,738, filed Jun. 14, 2005, the contents of all of which are incorporated herein by reference.

FIELD OF THE INVENTION

The present invention relates to a process for preparing atomoxetine hydrochloride.

BACKGROUND OF THE INVENTION

Atomoxetine HCl is a selective norepinephrine reuptake inhibitor. It is marketed under the name STRATTERA® for the treatment of Attention-Deficit/Hyperactivity Disorder (ADHD) and is available in 10 mg, 18 mg, 25 mg, 40 mg, and 60 mg dosage forms.

Atomoxetine, chemically known as (R)-(−)-N-methyl-3-(2-methylphenoxy)-3-phenylpropylamine; has the following structure:

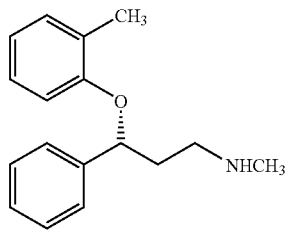

Atomoxetine, the (R)-(−) enantiomer of tomoxetine, is a aryloxyphenylpropylamine. It is about twice as effective as the racemic mixture and about nine times more effective than the (+)-enantiomer, as disclosed in U.S. Pat. No. 4,018,895 (assigned to Eli Lilly and Co.), EP 0 052 492 (Eli Lilly and Co.), and EP 0 721 777 (Eli Lilly and Co.).

Several processes for synthesizing 3-aryloxy-3-phenylpropylamines are known in the art. For example, U.S. Pat. No. 4,018,895 assigned to Eli Lilly and Co. discloses an aliphatic nucleophilic displacement of N-protected-3-halogen-3-phenylpropylamines by phenols, followed by N-deprotection. U.S. Pat. No. 4,868,344 assigned to Aldrich-Boranes, Inc. relates to the Mitsunobu reaction between 3-hydroxy-3-phenylpropylhalides and phenols, followed by amination of the resulting 3-aryloxy-3-phenylpropylhalides. Tomoxetine is also synthesized by the processes disclosed in U.S. Pat. No. 6,541,668 and WO 00/58262 (assigned to Eli Lilly and Co.) and WO 94/00416 (by Richter Gedeon Vegyeszeti Gyar RT). These documents disclose an aromatic nucleophilic displacement of an aryl halide by 3-hydroxy-3-phenylpropylamines under strongly basic conditions. The nucleophilic aromatic displacement process disclosed in WO 00/58262 includes reacting N-methyl-3-hydroxy-3-phenylpropylamine with a protected 2-fluorobenzaldehyde to produce tomoxetine after several functional group interconversion steps.

EP Patent No. 0 052 492 discloses a process for the preparation of atomoxetine HCl. In this process, (R)-(−)-tomoxetine (S)-(+)-mandelate is first basified in water to eliminate the mandelate, then extracted in diethyl ether. HCl gas is bubbled into the solution to obtain (R)-(−)-tomoxetine (atomoxetime) hydrochloride. Yields are reported as approximately 77%-90%.

Similarly, U.S. Pat. No. 6,541,668, assigned to Eli Lilly and Co., discloses a process for the preparation of atomoxetine HCl involving basifying the mandelate salt, followed by extracting with t-butyl methyl ether, removing water by azeotropic distillation, and adding hydrogen chloride. This process is inefficient due to long process time, low product yields, and the use of hazardous solvents that are incompatible with large-scale industrial synthesis.

Thus, there is a need in the art for processes for the preparation of atomoxetine hydrochloride that will produce higher yields and that will facilitate commercial production.

SUMMARY OF THE INVENTION

The present invention provides improved processes for the preparation of atomoxetine hydrochloride under reaction conditions that improve reaction yields and facilitate commercial synthesis. In particular, the invention is directed to the synthesis of atomoxetine HCl comprising:

a) combining a mixture of (R)-(−)-tomoxetine (S)-(+)-mandelate with an organic solvent to obtain a reaction mixture;

b) combining the reaction mixture with HCl to obtain atomoxetine HCl; and c) recovering atomoxetine HCl.

In another aspect, the present invention provides a process for preparing atomoxetine HCl comprising:

a) combining a mixture of (R)-(−)-tomoxetine (S)-(+)-mandelate and an organic solvent in the presence of water and a base to obtain a reaction mixture;

b) combining the reaction mixture with HCl to obtain atomoxetine HCl; and c) recovering the atomoxetine HCl.

Preferably, the amount of water is about 3 to about 7 ml per 1 gram of the starting material. Most preferably, the amount of water is about 5 ml per 1 gram of the starting material.

In yet another aspect, the present invention provides a process for preparing atomoxetine HCl comprising combining N-methyl-3-hydroxy-3-phenylpropylamine with 2-fluorotoluene in the presence of about 0.1 to about 20 moles DMSO and an alkali metal hydroxide to obtain a tomoxetine racemate, separating the desired (R)-(−)-tomoxetine from the (S)-(+)-tomoxetine in a (S)-(+)-mandelate form; and reacting the mandelate with HCl to obtain atomoxetine HCl.

DETAILED DESCRIPTION OF THE INVENTION

As used herein the term "aromatic solvent" refers to a $C_{6-10}$ aromatic hydrocarbon such as but not limited to benzene, xylene, or toluene.

As used herein, "room temperature" is meant to indicate a temperature of about 18-25° C., preferably about 20-22° C.

The present invention provides improved processes for the preparation of atomoxetine under reaction conditions that improve reaction yields and facilitate the process. In particular, the present invention is directed to the synthesis of atomoxetine hydrochloride by combining a mixture of (R)-(−)-tomoxetine (S)-(+)-mandelate and an organic solvent with HCl.

By producing atomoxetine HCl by direct displacement of (S)-(+)-mandelic acid by hydrochloric acid, it is believed that the processes of the present invention are more efficient than those disclosed in prior art. It is further believed that the processes of the present invention produce atomoxetine HCl in high yields, for example about 85 to about 95%. Furthermore, for embodiments that use (R)-(−)-tomoxetine (S)-(+)-mandelate in an enantiomeric ratio higher than 99:1, the enantiomeric excess of the atomoxetine HCl obtained is expected to be higher than 98%. The processes of the present invention preferably avoid the use of solvents that may be harmful to the environment, such as ethers and dichloromethane, which are required in some prior art processes for the preparation of atomoxetine HCl, such as the processes disclosed in EP Patent No. 0 052 492.

In one embodiment, a process is provided for the synthesis of atomoxetine HCl comprising combining (R)-(−)-tomoxetine (S)-(+)-mandelate and an organic solvent to obtain a reaction mixture, followed by combining the reaction mixture with HCl, either as a gas or an aqueous solution, to obtain a slurry. Preferably, the temperature is maintained at about 15° C. to about 20° C. when HCl is added. The slurry is maintained, preferably by stirring, for a sufficient time to obtain atomoxetine HCl, which is then recovered.

Another embodiment of the present invention provides a process for preparing atomoxetine hydrochloride, comprising providing a mixture containing (R)-(−)-tomoxetine (S)-(+)-mandelate, an organic solvent and water, and combining the mixture with a base to obtain a biphasic system. Preferably, the amount of water is about 3 to about 7 ml per 1 gram of the starting material. Most preferably, the amount of water is about 5 ml per 1 gram of the starting material. Preferably, the base is selected from the group consisting of NaOH, KOH, $Na_2CO_3$ and $K_2CO_3$. Most preferably, the base is NaOH. After the phases are separated, HCl is added, either as gas or as an aqueous solution. Preferably, prior to adding HCl, the water content of the organic phase is less than about 1%. It is also preferred that the temperature is maintained at about 15° C. to about 20° C. when HCl is added.

Preferably the organic solvent used in the processes described above for preparing atomoxetine hydrochloride is selected from the group consisting of aliphatic or aromatic hydrocarbons such as $C_{5-8}$ alkanes, toluene and xylene, $C_{1-4}$ alkyl esters such as methyl acetate, ethyl acetate, n-butyl acetate and iso-butyl acetate, ketones such as acetone, methyl-ethyl ketone, linear or branched $C_{1-4}$ alcohols such as methanol, ethanol and isopropanol and mixtures thereof. Most preferably, the organic solvent is selected from the group consisting of ethyl acetate, n-butyl acetate, and iso-butyl acetate.

In a particular embodiment, the present invention includes a process for the preparation of atomoxetine hydrochloride comprising the following steps:

a) combining N-methyl-3-hydroxy-3-phenylpropylamine with dimethylsulfoxide (DMSO) in the presence of an alkali metal hydroxide to form a slurry;

b) adding 2-fluorotoluene to the slurry to obtain a reaction mixture;

c) heating the resultant mixture to obtain tomoxetine;

d) combining the obtained tomoxetine with a $C_{1-4}$ alcohol, an aromatic solvent, and (S)-(+)-mandelic acid, e) heating the mixture to a temperature of about 60° C. to about 80° C.;

f) crystallizing (R)-(−)-tomoxetine (S)-(+)-mandelate from the reaction mixture;

g) adding an organic solvent, water, and a base to the salt of step f);

h) combining the mixture of step g) with HCl to form atomoxetine hydrochloride; and i) recovering the atomoxetine hydrochloride.

In a preferred embodiment, the resultant mixture in step c) is heated to a temperature of about 80° C. to about 145° C. Preferably, when the amount of the alkali metal hydroxide added in step a) is about 3 mole equivalents per mole equivalent of N-methyl-3-hydroxy-3-phenylpropylamine, the resultant mixture is heated to a temperature from about 135° C. to about 145° C. Preferably, when the amount of the alkali metal hydroxide added in step a) is about 5 mole equivalents per mole equivalent of N-methyl-3-hydroxy-3-phenylpropylamine, the resultant mixture is heated to a temperature of about 80° C. to about 100° C.

Preferably, the amount of DMSO is about 0.1 to about 20 moles per moles of N-methyl-3-hydroxy-3-phenylpropylamine, and the preferred base is KOH. The mixture obtained in step (a) is maintained preferably by heating mixture to a temperature from about 80° C. to about 150° C., to obtain racemic tomoxetine.

Alternatively, step g) may be performed in the presence of an organic solvent only.

Prior to step g), the obtained (R)-(−)-tomoxetine (S)-(+)-mandelate may be recrystallized from a solution comprising an aromatic solvent and a $C_{1-4}$ alcohol.

The reaction mixture obtained in step (f) may be a biphasic system. In this case, the two phases may be separated, and the HCl in step h) may be added to the organic phase.

Atomoxetine HCl may be separated from the reaction mixture by techniques known in the art, such as filtration. The product may be washed with an organic solvent. The product may then be dried, preferably under reduced pressure.

A preferred $C_{1-4}$ alcohol is methanol. Preferably, the aromatic solvent is toluene.

To increase the yield of the above process, the (S)-(+)-tomoxetine in the solvent mixture ("mother liquor," from which (R)-(−)-tomoxetine (S)-(+)-mandelate was obtained) may be racemized by combining an aprotic dipolar solvent and a base having a highly ionic counter ion. Preferably, the mixture is heated. Step (d) is repeated to further resolve the (R)-(−)-tomoxetine (S)-(+)-mandelate. Moreover, the present invention provides a process for preparing a pharmaceutical composition comprising R(−)-tomoxetine (atomoxetine) or a pharmaceutically acceptable salt thereof, which comprises bringing R(−)-tomoxetine (atomoxetine) or a pharmaceutically acceptable salt thereof into contact with one or more pharmaceutically acceptable carriers or excipients.

Having described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. All references mentioned herein are incorporated in their entirety.

EXAMPLES

Achiral HPLC analysis
Instrument: HPLC Hewlett Packard VWD detector HP1100
Column: YMC ODS-AQ 250 mm×4.6 mm (i.d.) cod. AQ-303
Mobile phase: $NaH_2PO_4$ 0.02M pH 3
Buffer: acetonitrile gradient
Flow: 1.5 ml/min
Temperature: 40° C.
Wavelength: 215 nm Chiral HPLC analysis
Instrument: HPLC Hewlett Packard VWD detector HP1100
Column: CHIRACEL OD-R cellulose tris (3,5-dimethylphenylcarbamate)
250 mm×4.60 mm×10 mm (Daicel Chemicals cat. N° DAIC14625)
Mobile phase: KPF6 100 mM/Acetonitrile—60/40
Flow: 0.8 ml/min
Temperature: 35° C.
Wavelength: UV, 215 nm

Example 1

(R,S)-N-methyl-3-(2-methylphenoxy)-3-phenylpropylamine (Tomoxetine Synthesis)

1100 g (14.1 mol) of dimethylsulfoxide, 200 g (1.21 mol) of N-methyl-3-hydroxy-3-phenylpropylamine and 221 g (3.63 mol) of potassium hydroxide (bulk industrial grade, 92.1% assay) were heated under stirring at 110° C. The mixture was then concentrated by vacuum distillation until about 130 g of solvent were removed. The mixture was allowed to cool to 80° C., then 400 g (3.63 mol) of 2-fluorotoluene were added. The mixture was heated to reflux (145° C.-147° C.) for one hour, and allowed to cool to about 90° C. 1000 ml of water and 1000 ml of toluene were added. The mixture was stirred for some minutes, at which time the phases were separated. The aqueous phase was extracted with 2×200 ml of toluene. The organic phases were collected and washed with 3×200 ml of water. Final organic phase weight: 1700 g. Tomoxetine content: 16.83% by weight (HPLC assay). Yield: 92.7%.

Example 2

(R)-(−)-Tomoxetine (S)-(+)-Mandelate (Tomoxetine Optical Resolution)

A solution in toluene of crude racemic tomoxetine (276.13 g, 1.081 mol, by HPLC assay) prepared as described in Example 1 was concentration in vacuum to remove water. The residue was taken up with 2025 ml of toluene and 26 ml of methanol. To the obtained solution 94 g (0.618 mol) of (S)-(+)-mandelic acid were added at 25° C. All solids were solubilized by heating to 65°-70° C. The crude mandelate salt was crystallized on cooling. The solid was isolated by filtration at 5°-10° C., washed with about 300 ml of toluene and dried in vacuo. Weight: 178 g. Tomoxetine content: 63.2% by weight (HPLC assay). Yield: 43.15%. Crude mandelate salt (R)-(−)-Tomoxetine enantiomeric ratio: R/S is about 95/5 (by chiral HPLC).

163 g of the obtained crude mandelate salt were re-crystallized from 489 ml of toluene and 49 ml of methanol as follows: the salt was solubilized by heating to 65°-70° C., then (R)-(−)-tomoxetine (S)-(+)-mandelate was crystallized on cooling, isolated by filtration at 5°-10° C., washed with about 2×90 ml of toluene and dried in vacuum. Weight: 153 g. Tomoxetine content: 63.97% by weight (HPLC assay). Yield: 38.7% from racemic tomoxetine. (R)-(−)-tomoxetine (atomoxetine) enantiomeric ratio: R/S>99/1 (by chiral HPLC).

Example 3

(R)-(−)-N-methyl-3-(2-methylphenoxy)-3-phenylpropylamine hydrochloride (Atomoxetine Hydrochloride)

27.88 g (0.0684 mol) of (R)-(−)-tomoxetine (S)-(+)-mandelate were mixed under stirring with 138 ml of ethyl acetate and 138 ml of water. 10.89 g (about 0.08 mol) of 30% aqueous sodium hydroxide were added. The phases were then separated. The organic phase was washed with 2×47 ml of water, then it was refluxed (73°-74° C.) with a Dean-Stark condenser until water content was below 1%. Keeping the temperature between 18° C. and 20° C. by means of water-ice bath cooling, 7 g (0.07 mol) of aqueous 36% hydrogen chloride was dropped into the solution under stirring. The hydrochloride then crystallized. The obtained suspension was stirred between 18° C. and 20° C. for one hour, the solid was collected by filtration, washed with 2×10 ml of ethyl acetate and dried in vacuum. Tomoxetine hydrochloride content: >99% by HPLC assay. Weight: 16.75 (0.0575 mol) g. Yield: 84%. Atomoxetine hydrochloride enantiomeric ratio: R/S>99/1 (by chiral HPLC).

Example 4

(R)-(−)-N-methyl-3-(2-methylphenoxy)-3-phenylpropylamine hydrochloride (Atomoxetine Hydrochloride)

45 g (0.110 mol) of (R)-(−)-tomoxetine (S)-(+)-mandelate were mixed under stirring with 225 ml of toluene and 225 ml of water. Keeping the temperature at about 40° C. by means of gentle heating, 21 g (about 0.16 mol) of 30% aqueous sodium hydroxide were added. The phases were then separated. The organic phase was washed with 100 ml of 1% aqueous sodium hydroxide, then filtered on paper and concentrated in vacuum to give 29.67 g of an oil containing 26.8 g of tomoxetine (by HPLC assay).

23.5 g of the oil were dissolved in 211 ml of ethyl acetate under stirring then, keeping temperature between 12° C. and 18° C. by means of water-ice bath cooling; gaseous hydrogen chloride was bubbled into the solution until acid reaction of litmus paper. The hydrochloride then crystallized. The obtained suspension was stirred at about 15° C. for one hour, then the solid was collected by filtration, washed with ethyl acetate and dried in vacuo. Tomoxetine hydrochloride content: >99% by HPLC assay. Weight: 24.3 g (0.0832 mol). Yield: 95%. Atomoxetine hydrochloride enantiomeric ratio: R/S>99/1 (by chiral HPLC).

Example 5

(R)-(−)-N-methyl-3-(2-methylphenoxy)-3-phenylpropylamine hydrochloride (Atomoxetine Hydrochloride)

5.17 g (0.01267 mol) of (R)-(−)-tomoxetine (S)-(+)-mandelate were mixed at room temperature with 25.5 ml of n-butyl acetate (and 0.6 ml of toluene added to simulate use of wet (R)-(−)-tomoxetine (S)-(+)-mandelate) under stirring. Keeping the temperature between 18° C. and 20° C. by means of water-ice bath cooling, 1.4 g of aqueous (36.4% w/w) hydrogen chloride was added into the obtained slurry. The slurry was stirred for 1 hour at room temperature, the solid was then collected by filtration, washed with 6 ml of n-butyl acetate and dried in vacuum. Tomoxetine hydrochloride content: >99% by HPLC assay. Weight: 2.95 g (0.01011 mol). Yield: 79.7%. Atomoxetine hydrochloride enantiomeric ratio: R/S>99/1 (by chiral HPLC)

Example 6

(R)-(−)-N-methyl-3-(2-methylphenoxy)-3-phenyl-propylamine hydrochloride (Atomoxetine Hydrochloride)

7.0 g (0.01718 mol) of (R)-(−)-tomoxetine (S)-(+)-mandelate were mixed at room temperature with 70 ml of ethyl acetate under stirring. Keeping the temperature between 15° C. and 20° C. by means of water-ice bath cooling, gaseous hydrogen chloride was bubbled into the obtained slurry until the congo red indicator paper became blue. The slurry was stirred for 2 hours at room temperature, the solid was then collected by filtration, washed with 3×10 ml of ethyl acetate and dried in vacuum. Tomoxetine hydrochloride content: >99% by HPLC assay. Weight: 4.86 g (0.01665 mol) g. Yield: 97%. Atomoxetine hydrochloride enantiomeric ratio: R/S>99/1 (by chiral HPLC)

Example 7

(R)-(−)-N-methyl-3-(2-methylphenoxy)-3-phenyl-propylamine (Atomoxetine Base Solution)

40 g (0.08697 mol) of (R)-(−)-tomoxetine (S)-(+)-mandelate (88.6% w/w by potentiometric assay) were mixed under stirring with 177.2 ml of n-butyl acetate and 177.2 ml of water. Keeping temperature at 23° C., 17.7 g (about 0.133 mol) of 30% aqueous sodium hydroxide were added. The phases were then separated. The organic phase was washed twice with 35 ml of water each time, then filtered on paper and used as it is for the next step.

Example 8

(R)-(−)-N-methyl-3-(2-methylphenoxy)-3-phenyl-propylamine hydrochloride (Atomoxetine Hydrochloride)

Under stirring and maintaining temperature between 22° C. and 25° C. by means of water bath cooling, 10.07 g (0.09945 mol) of aqueous hydrogen chloride (36%) were dropped on 177 g (0.08648 mol) of atomoxetine base solution (n-butyl acetate), prepared as in Example 7. The hydrochloride then crystallized. The obtained suspension was stirred at about 25° C. for one hour. The solid was collected by filtration and washed twice with 30 ml of n-butyl acetate each time. The solid collected was dried for 18 hours at 70° C. under vacuum. Tomoxetine hydrochloride content: >99% by HPLC assay.

Weight: 25.18 g (0.08629 mol). Yield: 99.8%. Atomoxetine hydrochloride enantiomeric ratio: R/S>99/1 (by chiral HPLC)

Example 9

Racemization of Unwanted Enantiomer

About 310 ml of the toluenic solvent mixture ("mother liquors") from optical resolution (e.g. Examples 2-4) were washed with about 50 ml of 2% aqueous sodium hydroxide, then concentrated under vacuum. The oily residue weighed 72.6 g and contained 51.29 g (0.20 mol) of tomoxetine (HPLC assay). 550 g (7.03 mol) of DMSO and 36.7 g (0.60 mol) of potassium hydroxide (bulk industrial grade, 92.1% assay) were added to the concentrate and the mixture was heated between 85° C. and 90° C. until optical rotation of the mixture decreased to 0.00 (3 hours). Heating was stopped, 300 ml of water and 300 ml of toluene were added. The mixture was stirred for some minutes, at which point the phases were separated. The aqueous phase was extracted with 50 ml of toluene. The organic phases were collected and washed with 3×80 ml of water, then concentrated under vacuum. Residue weight: 64.23 g. Tomoxetine content: 49.07 g (0.19 mol) (HPLC assay).

The residue was taken up with 392 ml of toluene and 2.9 ml of methanol, then 17.15 g (0.115 mol) of (S)-(+)-mandelic acid were added to the obtained solution at 25° C. All solids were solubilized by heating to 65°-70° C. The solution was cooled, crude mandelate salt crystallized, was isolated by filtration at 5°-10° C., washed with about 2×40 ml of toluene and dried in vacuum. Weight: 33.6 g. Tomoxetine content: 62.9% by weight (HPLC assay). Yield: 41.2%. Crude mandelate salt (R)-(−)-Tomoxetine enantiomeric ratio: R/S is about 95/5 (by chiral HPLC).

We claim:

1. A process for the preparation of atomoxetine hydrochloride comprising:
   a) combining (R)-(−)-tomoxetine (S)-(+)-mandelate with an organic solvent to obtain a reaction mixture comprising (R)-(−)-tomoxetine (S)-(+)-mandelate;
   b) combining the reaction mixture of step a) with HCl; and
   c) maintaining the reaction mixture of step (b) to form atomoxetine hydrochloride.

2. A process for the preparation of atomoxetine hydrochloride comprising:
   a) combining (R)-(−)-tomoxetine (S)-(+)-mandelate with an organic solvent in the presence of water and a base to obtain a reaction mixture;
   b) combining the reaction mixture of step a) with HCl; and
   c) maintaining the reaction mixture of step (b) to form atomoxetine hydrochloride.

3. The process of any one of claims 1 and 2, wherein the organic solvent is selected from the group consisting of aliphatic and aromatic hydrocarbons, $C_{1-4}$ alkyl esters, ketones, linear or branched $C_{1-4}$ alcohols, and mixtures thereof.

4. The process of claim 3 wherein the organic solvent is selected from the group consisting of $C_{5-8}$ alkanes, toluene, xylene, methyl acetate, ethyl acetate, n-butyl acetate, iso-butyl acetate, acetone, methyl-ethyl ketone, methanol, ethanol, isopropanol, and mixtures thereof.

5. The process of claim 4 wherein the organic solvent is selected from the group consisting of ethyl acetate, n-butyl acetate, and iso-butyl acetate.

6. The process of any one of claims 1 and 2 wherein step b) is carried out at a temperature of about 15° C. to about 20° C.

7. The process of any one of claims 1 and 2 wherein the HCl combined in step b) is either a gas or an aqueous solution.

8. The process of claim 2 wherein, prior to step b), the organic phase is separated from the aqueous phase and HCl is combined with the separated organic phase.

9. The process of claim 2 wherein the amount of water added is about 3 to about 7 ml per gram of (R)-(−)-tomoxetine (S)-(+)-mandelate.

10. The process of claim 9 where the amount of water added is about 5 ml per gram of (R)-(−)-tomoxetine (S)-(+)-mandelate.

11. The process of claim 2 where the base is selected from the group consisting of potassium hydroxide, sodium hydroxide, $Na_2CO_3$, and $K_2CO_3$.

12. The process of claim 11 where the base is sodium hydroxide.

13. The process for the preparation of atomoxetine hydrochloride comprising:
    a) combining N-methyl-3-hydroxy-3-phenylpropylamine with dimethylsulfoxide (DMSO) in the presence of an alkali metal hydroxide to form a slurry;
    b) adding 2-fluorotoluene to the slurry to obtain a mixture;
    c) heating the resultant mixture to obtain tomoxetine;
    d) combining the obtained tomoxetine with a $C_{1-4}$ alcohol, an aromatic solvent, and (S)-(+)-mandelic acid,
    e) heating the mixture to a temperature of about 60° C. to about 80° C.;
    f) crystallizing (R)-(−)-tomoxetine (S)-(+)-mandelate from the reaction mixture;
    g) adding an organic solvent, water, and a base to the salt of step f);
    h) combining the mixture of step g) with HCl to form atomoxetine hydrochloride; and
    i) recovering the atomoxetine hydrochloride.

14. The process of claim 13 wherein the DMSO is present at about 0.1 to about 20 moles per mole of N-methyl-3-hydroxy-3-phenylpropylamine.

15. The process of claim 13 wherein the alkali metal hydroxide is combined in step a) in an amount of about 3 to about 5 molar equivalents per molar equivalent of the N-methyl-3-hydroxy-3-phenylpropylamine.

16. The process of claim 13 wherein the mixture in step c) is heated to a temperature from about 80° C. to about 145° C.

17. The process of claim 15 wherein 3 molar equivalents of said alkali metal hydroxide are used, and the mixture in step c) is heated to a temperature of about 135° C. to about 145° C.

18. The process of claim 15 wherein 5 molar equivalents of said alkali metal hydroxide are used, and the mixture in step c) is heated to a temperature of about 80° C. to about 100° C.

19. The process of claim 13 wherein the reaction mixture of step g) is a biphasic system where the HCl is added to the organic phase.

20. A process for preparing a pharmaceutical composition comprising atomoxetine hydrochloride, which comprises bringing atomoxetine hydrochloride prepared according to anyone of claims 1, 2 and 13 into contact with one or more pharmaceutically acceptable carriers or excipients.

21. The process for the preparation of atomoxetine hydrochloride comprising:
    a) combining N-methyl-3-hydroxy-3-phenylpropylamine with dimethylsulfoxide (DMSO) in the presence of an alkali metal hydroxide to form a slurry;
    b) adding 2-fluorotoluene to the slurry to obtain a mixture;
    c) heating the resultant mixture to obtain tomoxetine;
    d) combining the obtained tomoxetine with a $C_{1-4}$ alcohol, an aromatic solvent, and (S)-(+)-mandelic acid,
    e) heating the mixture to a temperature of about 60° C. to about 80° C.;
    f) crystallizing (R)-(−)-tomoxetine (S)-(+)-mandelate from the reaction mixture;
    g) adding an organic solvent without a base and water to the salt of step f);
    h) combining the mixture of step g) with HCl to form atomoxetine hydrochloride; and
    i) recovering the atomoxetine hydrochloride.

22. The process of claim 1 wherein the (R)-(−)-tomoxetine (S)-(+)-mandelate and the organic solvent are combined without a base and water.

23. The process of claim 1 wherein atomoxetine hydrochloride is formed by direct displacement of (S)-(+)-mandelic acid by hydrochloric acid.

* * * * *